US008770750B2

(12) United States Patent
Vendel et al.

(10) Patent No.: US 8,770,750 B2
(45) Date of Patent: Jul. 8, 2014

(54) APPARATUS AND METHOD FOR ESTABLISHING AND/OR IMPROVING BINOCULAR VISION

(76) Inventors: Joar Vendel, Viken (SE); Michael Malmqvist, Viken (SE)

(*) Notice: Subject to any disclaimer, the term of this patent is extended or adjusted under 35 U.S.C. 154(b) by 0 days.

(21) Appl. No.: 13/513,135

(22) PCT Filed: Dec. 2, 2010

(86) PCT No.: PCT/EP2010/068781
§ 371 (c)(1),
(2), (4) Date: Aug. 8, 2012

(87) PCT Pub. No.: WO2011/067361
PCT Pub. Date: Jun. 9, 2011

(65) Prior Publication Data
US 2012/0307203 A1    Dec. 6, 2012

Related U.S. Application Data

(60) Provisional application No. 61/266,170, filed on Dec. 3, 2009.

(30) Foreign Application Priority Data

Dec. 2, 2009 (EP) ..................... 09177794

(51) Int. Cl.
A61B 3/08 (2006.01)
A61B 3/02 (2006.01)

(52) U.S. Cl.
USPC ........................... 351/201; 351/203; 351/240

(58) Field of Classification Search
USPC ................................................ 351/200–203
See application file for complete search history.

(56) References Cited

U.S. PATENT DOCUMENTS

| 5,206,671 | A  | * | 4/1993  | Eydelman et al. ............ 351/203 |
| 6,364,485 | B1 | * | 4/2002  | Fateh ............................ 351/203 |
| 8,454,166 | B2 | * | 6/2013  | Fateh ............................ 351/246 |
| 2001/0050754 | A1 |  | 12/2001 | Hay |
| 2003/0214630 | A1 |  | 11/2003 | Winterbotham |
| 2006/0103808 | A1 |  | 5/2006  | Horie |

FOREIGN PATENT DOCUMENTS

WO   WO 2008/070683 A1   6/2008

OTHER PUBLICATIONS

U.S. registration No. H00293; Task et al, Jun. 2, 1987, see entire document.*
PCT/EP2010/068781 International Search Report dated May 3, 2011.

* cited by examiner

Primary Examiner — Jordan Schwartz
(74) Attorney, Agent, or Firm — Knobbe Martens Olson & Bear LLP

(57) ABSTRACT

An apparatus and method are disclosed that provide for establishing and/or improving binocular vision by adaptation of perceptual motor learning for the visual system of a patient suffering of a binocular vision disorder. The apparatus has a set of two units, one for respectively eye, for manipulation of a vision parameter of the visual presentation, e.g. picture, movie, image. To control the visual presentation on respectively unit a processing unit is connected. The processing unit is adapted to determine a boundary value of a first and/or second vision parameter for the first and/or second manipulation of the first and second unit, where binocular vision disappears for the patient. Furthermore, the processing unit controls at least one vision parameter by manipulating, including oscillating or fluctuating, it within a first range, the first range having a maximum value that is less than the boundary value, for the perceptual motor learning.

17 Claims, 9 Drawing Sheets

APPARATUS AND METHOD FOR ESTABLISHING AND/OR IMPROVING BINOCULAR VISION

Related Applications

This application is the U.S. National Phase under 35U.S.C. §371 of International Patent Application No. PCT/EP2010/068781, filed on Dec. 2, 2010, and published in English on Jun. 9, 2011 as WO 2011/067361, which claims priority to European Application No. 09177794.6, filed Dec. 2, 2009, and U.S. Provisional Application No. 61/266,170, filed on Dec. 3, 2009. The contents of these applications are expressly incorporated herein by reference in their entireties.

FIELD OF THE INVENTION

This invention pertains in general to the field of orthoptics. More particularly the invention relates to apparatus and methods for perceptual motor learning for the visual system of a person having an eye disorder, in particular a binocular vision disorder. Even more particularly, the invention relates to the field of establishing and/or improving binocular vision for a patient having such a binocular vision disorder.

BACKGROUND OF THE INVENTION

Many people with binocular vision disorders never have these binocular disorders improved to the fullest extent. Corrective lenses establish normal visual acuity for many people, but the underlying visual disorder persists. Lenses alone cannot compensate for some disorders.

If vision is poor or hampered in one or both eyes, fusion (the brain's ability to use both eyes together and thereby attain and maintain depth perception) cannot occur and ocular alignment is lost due to a partial loss of brain control.

Presently, treatment of binocular disorders such as decompensated phoria, strabismus, suppression, amblyopia and accommodative insufficiency, explained below, is accomplished through widely varying techniques. However, all these techniques may be improved, or at least alternative solutions are desirable in some cases.

A strabismus can be manifest or latent. A manifest strabismus is commonly just called a squint, strabismus or tropia and the visual axis are not directed towards a common object (as illustrated in FIG. 2). A latent strabismus is commonly called a heterophoria or just phoria. This is a deviation of the visual axis in which is only apparent when one eye is covered.

Most people have a phoria without the phoria causing inconvenience in their everyday life. However, if a person having a phoria is exposed to deviating situations, such as when the person is put under stress, becomes sick, or the demand on the visual system increases by other reasons, the vergence system might not overcome the phoria. Such reasons may comprise extended work with display devices, work in badly illuminated environments, etc. A decompensated phoria is then established, wherein a decompensated phoria can be classified as one or more of a) Convergence insufficiency—the person is not able to overcome the phoria in near vision by means of convergence and the baseline phoria is outwards; b) Convergence excess—the person is not able to overcome the phoria in near vision by means of divergence and the baseline phoria is inwards; c) Divergence excess—the subject is not able to overcome the phoria in distance vision by means of convergence and the phoria is outwards; d) Divergence insufficiency—the subject is not able to overcome the phoria in distance vision by means of divergence and the phoria is inwards.

If a decompensated phoria is left untreated, strabismus and suppression will start to develop, wherein suppression is a mechanism in which the brain suppresses the image from one eye to avoid diplopia, i.e., double vision. Visual capability thus established by the eye that is not suppressed may again be fully sufficient without causing a major inconvenience in these persons everyday life good, in particular if the suppressed eye is occluded, e.g. by means of an eye patch. However, if left untreated, the suppression may develop further to an amblyopia. An amblyopia is vision disorder of degraded visual capability which is present even though a suppressed eye is occluded. If amblyopia and/or strabismus is left untreated it may degrade into abnormal retinal correspondence. Abnormal retinal correspondence (ARC) is a means by the brain to establish an alternative binocular vision in which the fovea of the good eye starts to correspond with a point outside the fovea of the other eye. Normally this point is equally distanced from the fovea as the angle of the squint.

The field of vision training involves therapy to improve the aforementioned visual disorder conditions, such as decompensated phorias, strabismus, suppression and amblyopia. For providing such therapy, an eye specialist, such as an orthoptist, optometrist or ophthalmologist, may prescribe visual tasks to be practiced under controlled conditions. The treatment of strabismus is for instance aimed at: a) eliminating an existing amblyopia, and b) realigning the eyes to restore binocular perception. A treatment of decompensated phorias is provided to eliminate an eventual suppression and to increase the vergence reserves. In accommodative insufficiency the aim is to increase the accommodative ability.

In DE 10207839 an apparatus for biofeedback for strabismus treatment is disclosed. The disclosed apparatus makes use of two unique images, one for each eye. For the eye which visual axis is miss-aligned, the corresponding image is spatially moved in such a way that the alignment of the image is no longer mis-aligned with respect to the visual axis of the eye. However, the image will be detected at a different area of the retina of the miss-aligned eye and as the visual cortex is used to connect areas from both eyes to interpret the visual information. The miss-aligned eye to which such compensated images are presented then tries to redirect itself to achieve the desired mis-aligned position as before, where corresponding visual information is used to be detected to gain "normal" vision for the person. This means that the eye will try to compensate even more than under "normal" strabismus vision. Hence, the apparatus of DE 10207839 is not suited to provide a suitable therapy, such as perceptual motor learning.

In U.S. Pat. No. 4,756,305 a similar eye training device is disclosed that alters refractory viewing by adding a refractive element such as a prism. Then strength of prisms is gradually reduced over a long-term treatment. However, the strength of the prisms is only adjusted by a doctor. Between visits of the patient to the doctor, the prisms are locked in place. Further, the device of U.S. Pat. No. 4,756,305 is not suited to provide vision therapy where amblyopia is eliminated, and only tries to realign the eyes to restore binocular perception. As therapy is only adjustable by the doctor and times between visits may be long, this device is not well suited for the therapeutic purpose.

In US 2001/0050754 a method for treating amblyopia in children is disclosed. A pair of eyeglasses or goggles is provided with an electrically and selectively darkenable lens, such as am LCD lens, so that for selected portions of time, one or the other eye may be occluded. In one embodiment, circuitry for providing pulses of a selected width to one or both lenses is incorporated in the eyeglasses or goggles, with the lens associated with the deviating eye receiving a wider pulse than the lens associated with the other eye. Thus, the deviating eye is occluded for a longer period of time than the normal eye. In another embodiment, a computer is coupled to the eyeglasses or goggles, and is provided with a program of interest to the child which selectively occludes the deviating eye.

The application US 2001/0050754 discloses an advanced version of an eye-patch and is not suitable to provide binocular therapy, such as perceptual motor learning, as explained above.

In US 2003/0214630 an interactive occlusion system is disclosed, including software and hardware, for the treatment of amblyopia using virtual reality or other physically interactive or perceptually immersive three-dimensional or two-dimensional computer generated simulations, in which the patient's occlusion compliance and usage time during occlusive and non-occlusive periods can be precisely recorded and the patient's visual acuity can be accurately measured to be provided to the clinician, as well as the capacity for entering prescriptions and treatment plans for individual patients and restricting individual access to that patient's prescription and treatment plan while allowing non-occlusive operation of the system after the prescribed occlusion time or for non-patient users.

The system disclosed in US 2003/0214630 is also an occlusive device, only capable of selectively occluding the patient's amblyopic and non-amblyopic eye and it is therefore not suitable to provide binocular therapy, such as perceptual motor learning wherein two images are manipulated and spatially moved.

In WO2008/070683 a system, methods, and apparatuses for amblyopia and ocular deviation correction are disclosed. In one aspect, a system for amblyopia correction includes an image processing unit to identify a set of image parameters and, when, in operation, the image processing unit modifies a source visual content based on one or more of the set of image parameters to generate visual content and a visualization unit coupled to the image processing unit operable to receive visual content from the image processing unit, the visualization unit having a screen, when, in operation, the screen displays the visual content.

The system disclosed in WO2008/070683 works similar to standard therapy for improving binocular vision, wherein static images are employed, and therefore does not offer dynamic training. By using static images the system relies on that the patient is actively being involved in the training or exercises. The disclosed system is designed to treat amblyopia and not phoria.

Moreover, several large and cumbersome instruments are known for analyzing vision disorders, such as strabismus, amblyopia, myopia that is known as nearsightness, or accommodation disorders, Two of such devices are the VS-II Vision Screener and the Opthalmic Telebinocular, available from Keystone View, Davenport, Iowa. The Vision Screener occupies over one-half cubic foot of space, weighs more than ten pounds, and must be plugged into a wall outlet. It has a viewing head with a forehead rest and a lens system with one viewing distance of 15 inches and another of 6 meters, equivalent to optical infinity. Static targets on test slides are illuminated by reflected light. The vision screener tests for visual acuity, phorias, fusion, depth perception and color perception. Images for the left and right eye are successively presented on a rotating target drum. However, these systems support only methods for diagnosis of eye disorders and are not adapted to provide perceptual motor training or other therapy or treatment of the diagnosed visual disorders.

Thus, there is a need for an alternative, new or improved instrument and/or method that can be used for treatment of binocular disorders such as decompensated phoria, suppression, amblyopia, and/or strabismus.

Hence, an improved patient friendly medical system, apparatus and/or method, at least suitable for treatment of binocular disorders, would be advantageous and in particular an apparatus allowing for increased flexibility, cost-effectiveness, easy handling in particular by a home user and/or user friendliness would be advantageous. There is in particular a desire to provide such a system, apparatus and/or method for providing perceptual motor learning for the visual system of a patient having binocular vision disorder, in order to establish and/or improve binocular vision of the patient. The system, apparatus and/or method are desired to have a high patient acceptance, for instance thanks to an easy to use, desirably by a sub-conscious therapy provided. Further, a convenient way of monitoring a larger patient population, without the need of costly frequent visits to eye specialists, would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing an apparatus, a method, and a computer program according to the appended patent claims.

According to a first aspect an apparatus for establishing and/or improving binocular vision is disclosed, wherein the apparatus is adapted to provide perceptual motor learning for the visual system of a patient having a first and a second eye and a binocular vision disorder. The apparatus comprises a first unit for a first manipulation of at least one first vision parameter related to a visual presentation directed towards the first eye and a second unit for a second manipulation of at least one second vision parameter related to a visual presentation directed towards the second eye. A processing unit is controlling the first and second unit. The processing unit is adapted to provide or determine a boundary value of the first and second vision parameter for the first and/or second manipulation of the first and second unit, wherein binocular vision disappears for the patient at the boundary value. The processing unit is further adapted to control the first and/or second unit to manipulate, including oscillate or fluctuate, the first and/or second vision parameter within a first range when the patient is using the apparatus. The first range is of a maximum value that is less than the boundary value, for providing an advantageous perceptual motor learning.

According to a second aspect, a method for establishing and/or improving binocular vision is provided for providing perceptual motor learning for the visual system of a patient having a first and a second eye and a binocular vision disorder. The method comprises a first manipulating of at least one first vision parameter related to a visual presentation directed towards the first eye and a second manipulating of at least one second vision parameter related to a visual presentation directed towards the second eye. The method comprises further providing or determining a boundary value of the vision parameter for the first and/or second manipulation, where binocular vision disappears for the patient. The method comprises further also controlling the manipulating, including oscillation or fluctuating, of the first and/or second vision parameter within a first range, wherein the first range has a maximum value that is less than the boundary value, for the perceptual motor learning.

According to a further aspect, a computer program that comprises a plurality of code segments is provided. The code segments are provided a first manipulation of at least one first vision parameter related to a visual presentation directed towards the first eye of a patient and a second manipulation of at least one second vision parameter related to a visual presentation directed towards the second eye of the patient. The computer program further comprises code segments for controlling the manipulation, including oscillation or fluctuation, of the first and/or second vision parameter within a first range, wherein the first range has a maximum value that is less than the boundary value, for the perceptual motor learning. Wherein the boundary value is determined previously and wherein the boundary value is a boundary value of the first vision parameter for the first manipulation and/or the second vision parameter of the second manipulation, where binocular vision disappears for the patient.

Further embodiments of the invention are defined in the dependent claims, wherein features for the second and subsequent aspects of the invention are as for the first aspect mutatis mutandis.

The term "oscillate" as used in the context of the present application means to move or swing from side to side regularly; or to cause to move to and fro; or vibrate; or to vary between alternate extremes; or to waver between, courses of action, etc; or to undergo or produce or cause to undergo or produce oscillation. This could be applied to all vision parameters for example how to fade color/contrast/focus/light level in or out or how images are spatially moved in relation to each other.

The term "fluctuate" as used in the context of the present application means to change or cause to change position constantly; or be or make unstable; or waver or vary; or to change continually; or shift back and forth; or vary irregularly; or to move back and forth in waves. This could be applied to all vision parameters for example how to fade color/contrast/focus in or out or how images are spatially moved in relation to each other.

The terms "fluctuating" or "oscillating" as used in the context of the present application means to actively exerting an influence on an entity, in operation changing, in particular during a single continuous occasion, such as a training or therapy session. These definitions of the terms "fluctuating" or "oscillating" thus stands in contrast to what is understood as e.g. statically, i.e. not moving, or fixed.

The term "vision parameter" as used in the context of the present application means a typical value of a visual presentation that is controllable in its way it is presented to at least one eye. Vision parameters are controllable and comprise e.g. focus, brightness, color of a visual presentation as long as these vision parameters influence binocular vision to the extent that these vision parameters contribute at least partly to establish binocular vision. Manipulation of such vision parameters thus comprises defocus, fading, color change, intensity change, illumination change, etc. In certain particularly preferred embodiments, vision parameters comprise spatial parameters including dimension or position of an image. Manipulation of such vision parameters may thus comprise inducing a movement, displacement, rotation, position, size or other types of spatial operation of the visual presentation, e.g. of an image presented on one or more screens. Manipulation of such vision parameters may in some embodiments be made of the entire visual presentation respectively. Alternatively or in addition, such vision parameters are modified only in a portion of such visual presentation in some embodiments.

The term "establish" as used in the context with establishing binocular vision of the present application means to cause, create, start, initiate, or bring about binocular vision of a patient that previously lacks binocular vision. The term "improving" as used in the context with improving binocular vision of the present application means to ameliorate, make better, or achieve a better binocular vision of a patient that already has a binocular vision, but which might be improved, such as patients having a phoria (latent strabismus) that needs to be compensated. The term "establishing and/or improving binocular vision" as used in the context of the present application consequently means one of a) establishing, b) improving, or c) establishing and (then) improving binocular vision.

Visual presentations may e.g. be based on image data, such as when displayed on a screen. Alternatively, the visual presentation may have a basis in real illuminated objects presented to the eye, wherein vision parameters of the visual presentation are modifiable by optical means, e.g. spectacles that have controllable refractivity, tinting, color, etc.

Embodiments provide training of the visual cortex in order to achieve a substantially evenly matched eye vision of both eyes processed by the visual cortex. A visual presentation is provided to the eyes within the Panum's fusional space 10 (FIG. 1), i.e., with a slight variation in disparity. In some embodiments vergence eye movements are introduced to the person not being aware of the induced variation and the persons vergence capability will increase with continued training. Thus, when a patient has unequal perceptive intensity for the two eyes, suppression and amblyopia are treated in embodiments by means of forcing the person to use the suppressed or amblyopic eye. For instance by image manipulation, a unique situation is provided for individuals with an eye disorder as each eye is provided with an image of controlled unique vision parameters, like size, position, blurriness, etc., to interpret in the visual cortex. As respectively of the two eyes is presented with unique images, the brain, i.e. more precisely the visual cortex, becomes involved to align the visual impression from each eye to obtain an aggregated comprehensive understanding. By changing and/or manipulating different image vision parameters differently for each eye, a unique situation is provided where the patient is enabled to exercise the visual cortex. In some embodiments even the ocular muscles are involved in this training to some extent, when the modified vision parameter is a spatial parameter of the image or visual presentation. However, exercise in the present context should not be confused with purely physical training of ocular muscles. In some embodiments the ocular muscles are substantially not engaged, for instance when changing the blurriness of one of the images to force the aforementioned use of the suppressed or amblyopic eye. For situations where both sensational and motoric capabilities are to be coordinated by an individual to achieve a new, higher or elevated skill or ability, improved perceptual motor learning is provided by embodiments of the invention.

Some embodiments of the invention provide for improved patient compliance, i.e. the patient performing training without being aware of the training being made.

Some embodiments of the invention provide for determination of the initial diagnosis was correct, incorrect or incomplete, depending on evolvement of improvement in binocular vision. No improvement may imply that the initial diagnosis was incorrect or incomplete whereby the patient can be sent to an optician, a MD or a responsible therapist.

Some embodiments of the invention provide for training separated from patient activity, no interaction is necessary during training other than a visual contact with a visual presentation. The training may be combined with other optical measurements.

Some embodiments of the invention also provide for subliminal, sub-conscious, training and/or exercises. The patient is commonly not deliberately training or exercising; the patient is watching a visual presentation, which contents as such are attracting the attention of the patient. Such presentations that attract the attention of the patient are for instance movies, interesting presentations, entertaining presentations, and/or games, such as computer games. The presentations may be two-dimensional (2-D) or three-dimensional (3-D) stereoscopic presentations. Some embodiments are independent of such contents of the visual presentation as such.

Some embodiments of the invention provide for a feedback of the effectivity of training and provide thus for a control of the training effectivity. By the feedback of the progress of the therapy monitoring the effectiveness of the training is provided. Efficiency of an ongoing therapy is measured from available data, for example: when training was made; how long time training is ongoing; how quickly subject gets tired from training etc. "Cheating" by lazy subjects not performing the training or subjects not performing the training correctly is therefore detectable and can be avoided.

Some embodiments provide for training of patients, such as young persons or children, without substantially boring or tiring the patients during training sessions, e.g. when playing a computer game or watching a movie.

Some embodiments provide for a feedback from the patient that they consciously follow the visual presentation, e.g. by an ongoing computer game. This ensures that the unconscious training is reliably performed without a patient evading the training.

Some embodiments provide for training in an environment that is convenient for the patient, e.g. at home. Thus the issue is overcome that training results may not be achieved when having to perform a test or training in a stressful environment, such as a clinical environment. Some embodiments of the invention provide for a reduction of visits of doctors and/or health care providers. Training or therapy may be provided in a home environment and doctor visits are only made when necessary.

Some embodiments provide for training or therapy independent of the spatial position of the patient in relation to the visual presentation. The patient does not need to be fixated in an inconvenient position in relation to the visual presentation. As a boundary value is provided (e.g. from an optician for the specific patient) or determined at which binocular vision disappears for the patient for each specific session, the embodiments become independent of a need to determine or ensure a specific predetermined spatial fixation of the patient in relation to the visual presentation on which training is based.

Some embodiments of the invention also provide for a capability of the system to automatically indicate and/ or contact the health provider when so needed, e.g. when binocular vision is established and/or sufficiently improved.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF EMBODIMENTS OF THE INVENTION

Figure 1:
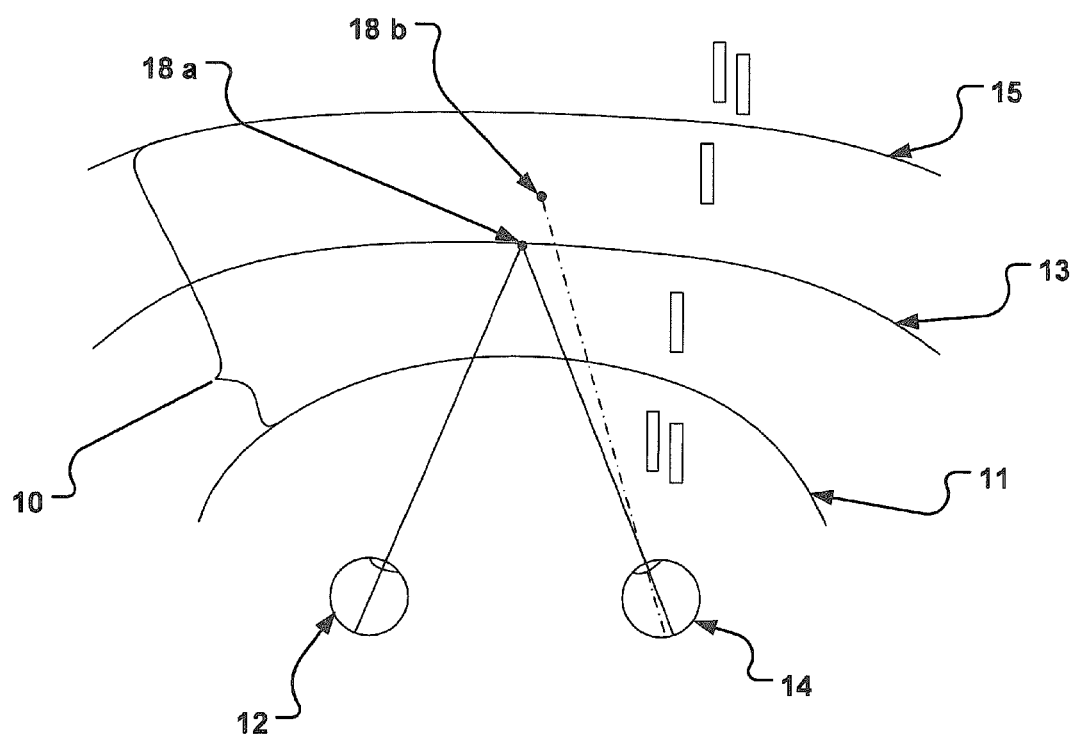
FIG. 1 is a schematic illustration of a slight misalignment of a visual axis which occurs in decompensated phorias and an illustration of the visual range, including the Panum's fusional space.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The Visual System and Disorders

At birth everybody has a squint (also called manifest strabismus, heterotropia or tropia). If the newborn develops normally this squint disappears within the first months of life. Thereafter, almost everybody has a phoria (also called heterophoria or latent strabismus/heterotropia/tropia/squint). This phoria is due to the physiological resting point of the eye within the ocular cavity is not identical to the visual axis being parallel. However, this phoria gives in most people not rise to any problems or symptoms. This is due to the vergence system of the eyes, i.e., the ocular motor systems ability to perform disjunctive eye movements—the vergence reserves, being able to overcome the angle of the deviation and thereby direct the eyes towards a common object of regard.

When the vergence reserves (or fusional reserves) for some reasons cannot overcome the phoria, the phoria gives rise to symptoms and asthenopia. The phoria is then called a decompensated phoria. Patients with a decompensated phoria will sometimes even see objects as double, which means that a squint is sometimes present. In addition to being called a decompensated phoria, this type of squint is also called an intermittent squint.

Young children who, for some reason, do not have equal retinal image quality may never gain binocular vision, i.e., they never get to the stage where the initial squint is overcome and becomes a phoria, and suppression and amblyopia starts developing directly. Amblyopia can, however, only develop during the critical period of visual development which is until the age of about 12-15 years of age. After that only suppression can develop.

On the other hand, binocular vision problems can also be caused by the accommodative system, i.e., the focusing system of the eyes. Some people have an accommodative system that is not able to fully focus the eyes and they suffer from accommodative insufficiency which yields symptoms of blurred images and asthenopia. Furthermore, some subjects with a high degree of hyperopia (the refractive error often called long sighted), who are not given refractive correction can develop a squint (with the later onset of suppression and amblyopia) since the accommodative system will try to overcome the refractive error. Since accommodation is linked with the vergence system, the accommodation used to overcome the hyperopia, will induce convergence of the eyes, and if this convergence cannot be offset by the vergence system, a tropia will be the consequence.

Many people with binocular visual disorders never have those disorders improved to the fullest extent. Corrective lenses establish normal visual acuity for many people, but the underlying visual disorder persists. Lenses alone cannot compensate for some disorders.

Decompensated phorias and accommodative insufficiency can be treated with visual therapy. This type of therapy is called orthoptics or orthoptic treatment. Orthoptic treatment is aimed at treating the vergence system's capability to rotate the eyes and the accommodative system's ability to change focus. Orthoptics can even be used to treat amblyopia and suppression. Strabismus can be treated through surgery. However, surgery is expensive, invasive, and has a surprisingly low rate of effectiveness. In addition over 85% of the operations do not provide effective treatment for strabismus. Most surgery simply treats strabismus cosmetically by physically reorienting the eyeball, but the patient is still not using both eyes together as a unit. Any underlying suppression or amblyopia which frequently accompanies strabismus remains untreated.

Amblyopia involves reduced vision in one eye, typically because of mental suppression. It is caused by inadequate visual stimulation of the brain during the critical period of visual development. Amblyopia is frequently induced by strabismus or by a high refractive error in only one eye. Primary strabismus leads to amblyopia through the neural mechanism of suppression, because the brain partially or completely ignores images coming from the crossed eye. Amblyopia results in poor visual efficiency due to decreased stereopsis and poor distance judgment. This condition is frequently treated by patching the good eye to force the brain to utilize the amblyopic eye. Recent studies indicate, however, that such treatment can induce amblyopia in the patched eye. About one-third of all persons with strabismus are diagnosed for amblyopia. Strabismus and amblyopia affect about 5% of the population.

Embodiments provide in particular for treatment of amblyopia, amongst other binocular vision disorders described herein.

The visual impression of an object detected by the eyes becomes decoded in the visual cortex in the back of the brain. The information gets processed in the visual cortex and for an observer having normal binocular vision superimposed information gets revealed, e.g. depth perception. For most observers having a binocular eye disorder this additional information does not fully develop, depending on the type of eye disorder and degree of severity of the same. For an observer having e.g. an amblyopic eye, otherwise known as lazy eye, decodes most of the visual impression from the other eye and consequently fails to benefit from additional binocular information. A strabismus observer will experience a similar situation.

Phoria problems are common complaints among patients in practice. They can present a history of tiredness when reading, asthenopia, diplopia (double vision) during near point tasks or trouble focusing from near to far. There can be various conditions limiting the ability to converge, such as changed vision demands, psychological factors and psychopharmacological drugs, under function of the extra ocular muscles or in more rare cases the cause is neurological. Convergence insufficiency, is the most common type of decompensated phoria, and can mainly be found in patients with exophoria, but even esophoria, at near, though this is rare. The most common is an exophoric condition. Orthoptic therapy improves the near point of convergence (NPC) and the fusional vergence ability, i.e. the ability to control the phoria.

The components of the ocular-motor system, accommodation and vergence eye movements, are responsible for providing clear and single vision. FIG. 1 illustrates a person having a left eye 12 and a right eye 14. The horopter 13, and Panum's fusional space, 10 within which all objects are seen singly. Double vision, diplopia, occurs for objects outside the boarders of Panum's fusional space (11 and 15), as illustrated by the dual objects outside the Panum's fusional space in respect the single objects within the same. When having convergence problems the person is showing a remote near point of convergence (NPC). NPC is the nearest point where the patient reports that the target has become double or the examiner observes one eye losing fixation and turn outward/inward, whichever occurs first. NPC is conventionally measured with a RAF-ruler. Normal values of NPC range between 4 cm and 16 cm from the corneal plane. Values greater than 16 cm, which is to be considered as a reduced ability to converge, may give symptoms in near vision. However, in some studies it is considered desirable to be within the 10 cm limit. An observer having normal binocular vision who wishes to change fixation from a distant object to one near (or vice versa), then the retinal image of the target object is initially defocused (blur describes this error of focus) and there is a fixation error between the image of the target and the fovea (disparity refers to this error of fixation). In order to bring clarity to the retinal image the eye must focus in a process known as accommodation, and to overcome disparity the eyes must change vergence angle to maintain fixation within corresponding retinal areas (if non-corresponding points of the retina stimulated then double vision will result). In FIG. 1 the desired fixation point, 18a, for an observer having no eye disorder is seen as well as fixation point, 18b, of an observer having an eye disorder, thus showing an exophoric fixation disparity. Fixation disparity is a condition in which the visual axis does not intersect at the object of regard but that the object is still imaged within Panum's fusional space. Commonly the dominant eye is directed towards the object of regard and the fellow eye is directed slightly more convergent (in esophoric conditions giving rise to esophorix fixation disparity) or divergent (in exophoric conditions giving rise to exophoric fixation disparity). When fixation disparity occurs a person with compensated phorias will act upon the disparity to place the image of the object on corresponding retinal point, i.e., the disparity will be eliminated. Fixation disparity then serves as a cue to the final convergence or divergence movements of the eyes Accommodation is an involuntary adjustment of the eye to focus the image of an object on the retina. In accommodation for near vision, the ciliary muscle contracts to reduce tension on the lens and allow it to become steeper, that is, to become more convex. Several factors reduce the accommodative mechanism. During the normal aging process the lens becomes stiffer. Environmental, genetic and other factors can increase lens stiffness or weaken the ciliary muscle. These result in headaches and discomfort when working on near tasks such as reading or focusing on a computer screen.

Figure 2:
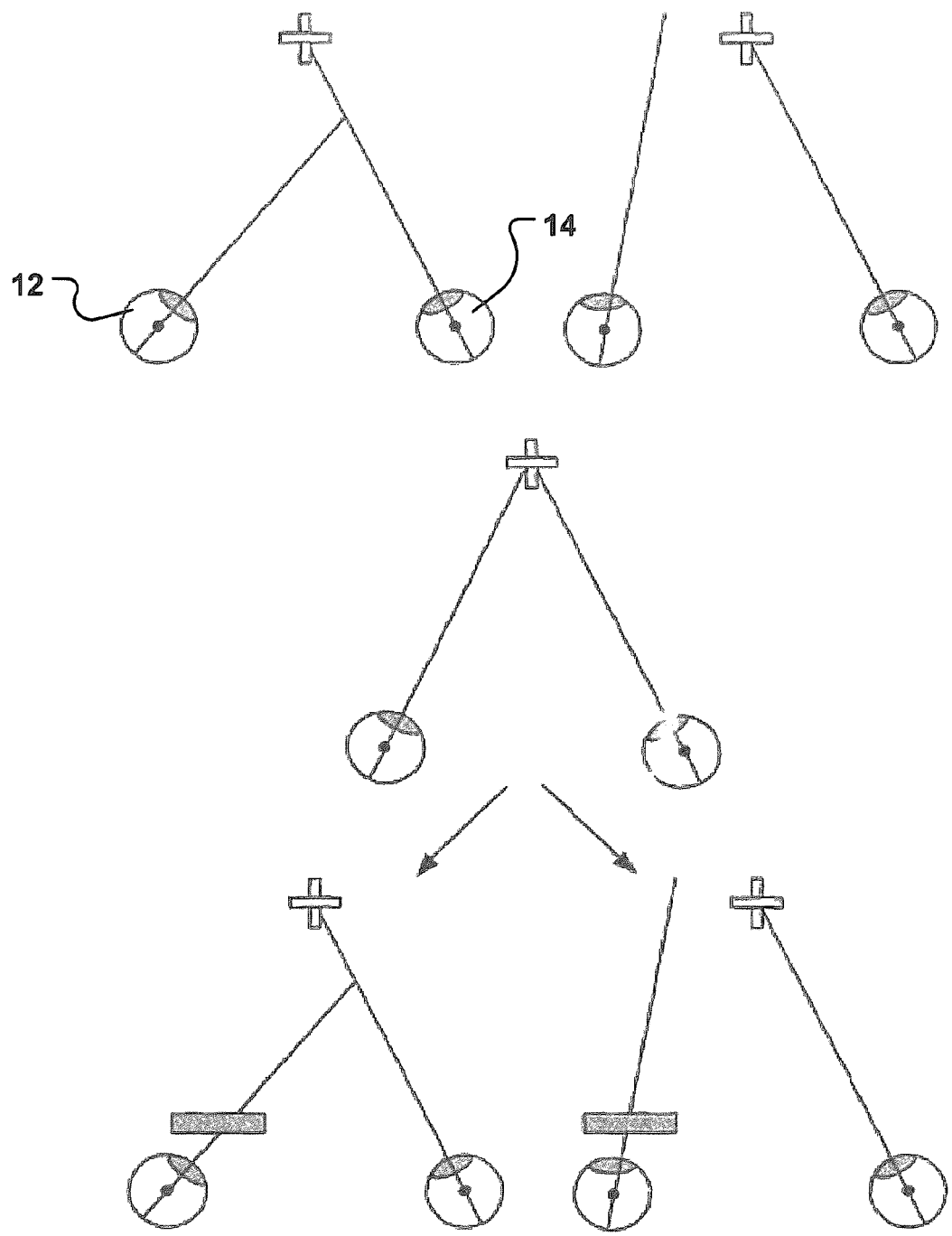
FIG. 2 is a schematic illustration of visual axis miss-alignments for developed strabismus (top); and suppressed strabismus detected with a cover test (bottom)

Binocular fixation of a stationary object requires that both visual axes are aligned with an object of interest in order to eliminate double vision, see FIG. 2 middle (e.g. no strabismus). Examination of the muscular and neurological systems involved in the coordination of the two eyes can be carried out using a cover test. The cover test consists of the covering and uncovering of each eye in turn while the fellow eye maintains fixation on a target. If no movement is seen of in either eye when the other eye is being covered demonstrates a phoria. In the case of a phoria the eye behind the cover will move either inwards (i.e., an esophoria is present, see FIG. 2 bottom left) or outwards (i.e., an exophoria is present, see FIG. 2 bottom right). Any movement of the eye when its fellow is being covered indicates the presence of heterotropia (commonly referred to as strabismus or squint), as seen in FIG. 2 top. Strabismus can either be convergent (esotropia) or divergent (exotropia) and can affect either eye, as illustrated in FIG. 2 top. For the purpose of illustration FIG. 2 top left shows a left esotropia and top right shows a left extropia. The primary sensory effect of strabismus is amblyopia in the non-fixating eye. One of the consequences of amblyopia is an increased threshold for stereopsis. Strabismus can result from adaptive pressures being placed on a compromised binocular system.

As mentioned in the background section, the treatment of strabismus is aimed at: 1) eliminating suppression and amblyopia; and 2) realigning the eyes to restore binocular perception. Embodiments provide either for the first, the second or both of these treatments.

Conventionally, surgical treatment of strabismus is an intervention where the eye is re-positioned in the eye socket in a way to achieve aligned visual axes. However, by relocating the eye bulb in a sense chance the retina's position in relation to the observed object. Hence, will the impression of vision be miss-aligned in the visual cortex which may result in a loss of binocular vision, i.e. double vision. For some individuals the strabismus will re-establish itself over time due to the visual cortex is trying to align the visual impressions from the both eyes and by doing so the visual axis of the previous affected eye is change back, i.e. the visual information of the retinal image corresponds between the both eyes again.

There are two groups of methods used for treatment of amblyopia in strabismus and for non-surgical treatment of strabismus: occlusion methods and those using a biofeedback procedure. Until recently the most effective method for treatment of strabismic amblyopia was occlusion. This method is based on the occlusion of the dominant eye by patching and thereby forcing the crossed eye to perform the visual function. However, this method des not provide for a control of the ongoing therapy. With one patched eye, binocular vision is not possible and it is doubtful if an efficient training can be achieved by this conventional method, as already mention in the afore background section.

The biofeedback therapy method is a technique which is based on conditioning principles and has been used in a variety of applications. The technique provides a person with immediate information from the biological process which normally is beyond his conscious awareness, thus facilitating voluntary regulation of these same functions. The methods for vision correction based on a biofeedback procedure can be divided into two categories. The first method is targeted on the improvement of visual acuity of the eye with a misaligned optical axis. The methods falling in the second category use autotraining to develop endogenic reflectory mechanism in order to reduce the degree of optical axis misalignment in the crossed eye. Embodiments described below may be based on each of these two methods.

Methods for treatment of miss-alignment of visual axis are disclosed in U.S. Pat. No. 6,033,073. The visual training system disclosed comprises image viewing means, wherein the patient is hooked up to the training system both with electrooculogram electrodes and with electromyogram electrodes. During a session series of images are displayed and responses are measured via the different electrodes and analyzed to assess differences between the eyes. However, this visual training system is hardly suited for children due to the amount of electrodes used to get reliable results and the fact that children most often lose interest in training. Moreover, the system is not suited for home training based on the high level of experience demanded of a person applying electrodes to a third individual to get accurate result of the monitoring. At hospitals and/or neurophysiology departments these persons are highly specialized trained nurses. This directs use of the visual training system disclosed in U.S. Pat. No. 6,033,073 not to be used at homes because of potentially not reliable measurements.

The following description focuses on an embodiment of the present invention applicable to train a person with eye disorders and in particular to training persons affected by decompensated phoria or strabismus with suppression and amblyopia. However, it will be appreciated that the invention is not limited to this application but may in embodiments be applied to various other binocular vision disorders suitable for orthoptic treatment.

Embodiments target on training the visual cortex in order to achieve an evenly matched eye vision processed by the visual cortex: By showing images or visual presentations within the Panum's fusional space, i.e., with a slight variation in disparity, vergence eye movements are introduced to the person not being aware of the induced variation and the persons vergence capability will increase; and with unequal intensity for the two eyes presentation suppression and amblyopia can be treated in embodiments by means of forcing the person to use the suppressed or amblyopic eye. By image manipulation, as presented below, a unique situation is provided for individuals with an eye disorder as each eye is provided with a unique image to interpret in the visual cortex. As respectively of the two eyes is presented with a unique image, and thus the brain, i.e. the visual cortex, becomes involved to align the visual impression from each eye to obtain an aggregated comprehensive understanding. By changing and or manipulating different image parameters or vision parameters differently for each eye, a unique situation is provided where the patient is enabled to exercise the visual cortex, and in some extent even the ocular muscles involved. However, exercise in the present context should not be confused with purely physical training of muscles. For situations where both sensational and motoric capabilities are to be coordinated by an individual to achieve a new, higher or elevated skill or ability, perceptual motor learning is commonly used as a comprehensive concept.

Figure 3:
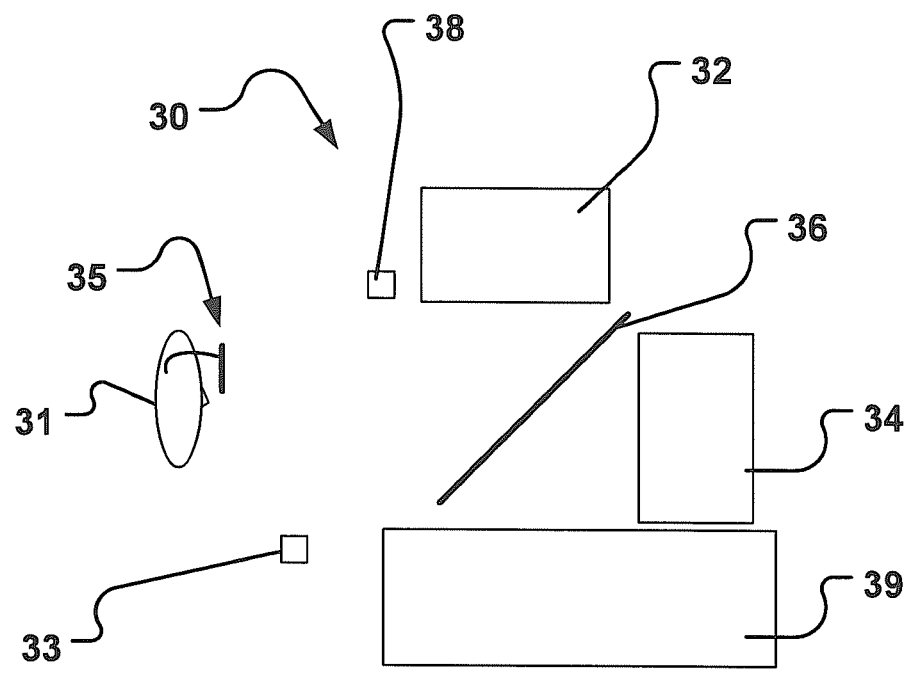
FIG. 3 is a lateral view of an embodiment showing an apparatus set-up.

An embodiment of the invention will be described according to a system or apparatus 30 shown in FIG. 3. However to substantiate the fundamental principle of the invention is not confined to this embodiment of a system configuration for visualization.

The system 30 comprises a first screen 32 and a second screen 34 with a semi-transparent mirror 36. The system 30 also has a processing unit 39, and a blocking device 35 in relation to a person or patient 31, and an input device 33 and optionally or additionally the system 30 comprises an eye tracking device 38. The embodied system 30 is thus computer based and may be adapted to perform certain methods of perceptual motor learning.

Figure 5:
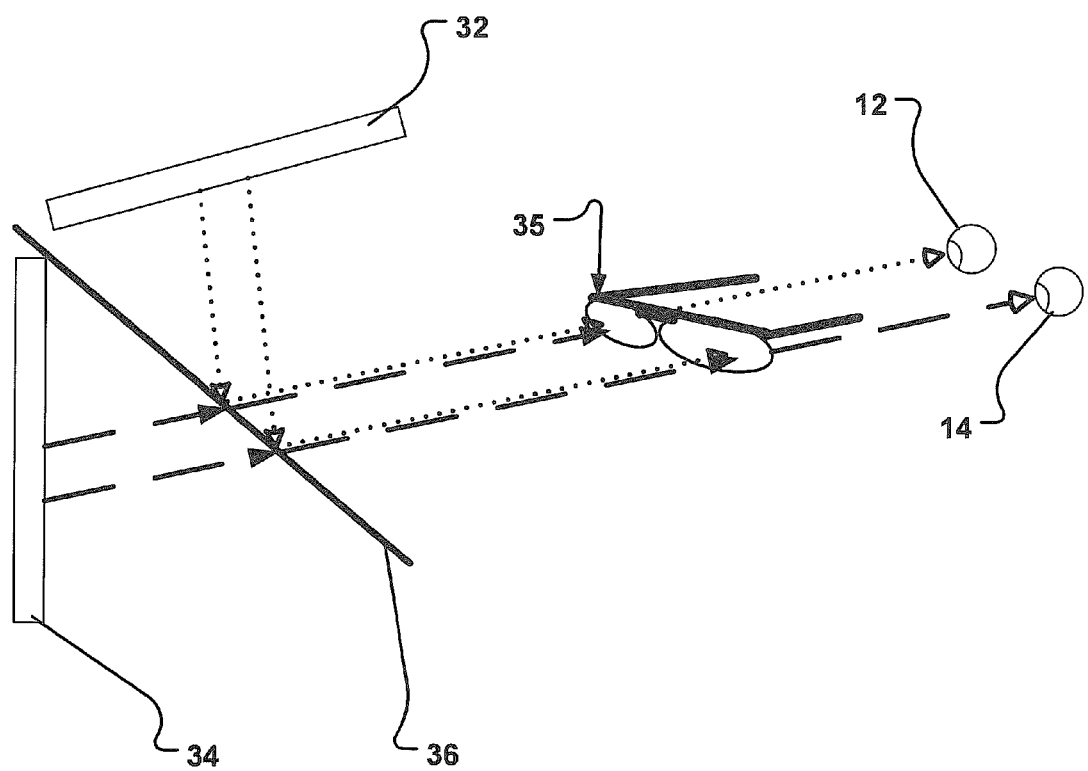
FIG. 5 is a perspective view of an embodiment, wherein an image is projected on a first screen and an optical path to a patient's eye is illustrated with a dotted line, and an analogous second screen and image is illustrated with a dashed line for the corresponding optical path.

The apparatus or visualization system is divided into a right hand-side part and a left hand-side part in respect to which vision field is affected, such as illustrated in FIG. 5. The processing unit 39 controls the visual presentations based on image data on the first screen 32 and the second screen 34. Each screen in this embodiment is covered with a polarized surface layer, exposing the images to the left and the right eye with the aid of the 50% reflective mirror 36. The blocking device 35 facilitates separation of visual presentations from the dual set of screens, i.e. blocking a visual presentation based on image data from either visual field to be visible by the not intended eye.

The separation of visual information from the visual presentations is further illustrated in FIG. 5 where the separation into a right hand-side part and a left hand-side part in is illustrated. The visual information from the first screen 32, illustrated by dotted line in FIG. 5, is reflected and diverted by the mirror 36 towards the patient's right eye 12 via the blocking device 35. The patient's left eye 14 simultaneously registers visual information from the second screen 34, illustrated by dashed line in FIG. 5, which is passing through the mirror 36 and the blocking device 35.

Moreover, the processing unit 39 is arranged to provide a predetermined visual effect beneficial for the treatment of the person suffering from an eye disorder, comprising a binocular vision disorder to be treated. In some embodiments of the apparatus the visual presentation based on image data in first and second visual fields is provided to fluctuate or oscillate in relation to each other to exercise the perceptual motor learning. The two image units or monitors and a mirror implement the principle of physiological diplopia to induce convergence in creating a computerized stereogram. This is the basis that can be adapted to different types of visual defects by the software. This adds range and variety to NPC exercises thus provided.

The first screen 32 and the second screen 34, display, monitor or image unit represents physical units to divide a visual presentation based on image data into a first visual field and a second visual field. The first visual field is e.g. aligned with the right eye 12 and the second is aligned with the left eye 14. However, some embodiments may utilize a single display unit to achieve such a separation of images into a first visual field and a second visual field. For these embodiments, such as 3-D screens having a single 3-D display, the reflective mirror may be omitted.

The apparatus 30 provides establishing and/or improving binocular vision by perceptual motor learning for the adaptation of the visual system of a patient suffering of a binocular vision disorder. The apparatus has a set of two units, i.e. the first screen 32 and the second screen 34—one for respectively eye, for manipulation of a vision parameter of the visual presentation, e.g. a picture, movie, or image. To control the visual presentation on respectively unit, the processing unit 39 is operatively connected thereto. The processing unit 39 is adapted to provide or determine a boundary value of at least one of a first vision parameter and a second vision parameter for the first and/or second manipulation of the first and second unit. The boundary value is the value of the at vision parameter where binocular vision disappears for the patient. Alternatively, a plurality of vision parameters may be modified to determine a multi dimensional field of these values which has a boundary border within which binocular vision is present and outside of which binocular vision is distorted. In the latter case, the boundary value is the aforementioned boundary border of the multi dimensional field. Furthermore, the processing unit 39 is adapted to control at least one of the vision parameters by oscillated or fluctuated manipulation within a first range on the first and/or second unit. The first range has a maximum value that is less than the boundary value, for the perceptual motor learning. This means that at least one vision parameter is actively changed, but kept in the first range, during a therapy session for at least one of the visual presentations. The vision parameter is changed to keep the patient vision within the Panum's fusional space. This means by showing images or visual presentations that are kept within the Panum's fusional space, the therapy is advantageously provideable by the present apparatuses and methods. This manipulation is described in more detail below.

Alternatively or additionally, the first screen 32 and the second screen 34 could each comprise at least one vision parameter to be manipulated. During a training session only one of these at least one vision parameters will be manipulated (including oscillated or fluctuated) e.g. spatially for each screen respectively. The other vision parameters will be kept constant.

To create a more challenging environment for the eyes during a training session, more than one of the at least one vision parameters could be varied or adjusted simultaneously e.g. to fade out the image for the dominant eye; or to fluctuate the fading, e.g. for the dominant eye, within a set range, determined by a boundary value. The manipulating of further vision parameters will overlap with e.g. spatial manipulation (i.e. fluctuation or oscillation) of at least a part of the images presented on the first screen 32 and the second screen 34.

Figure 4:
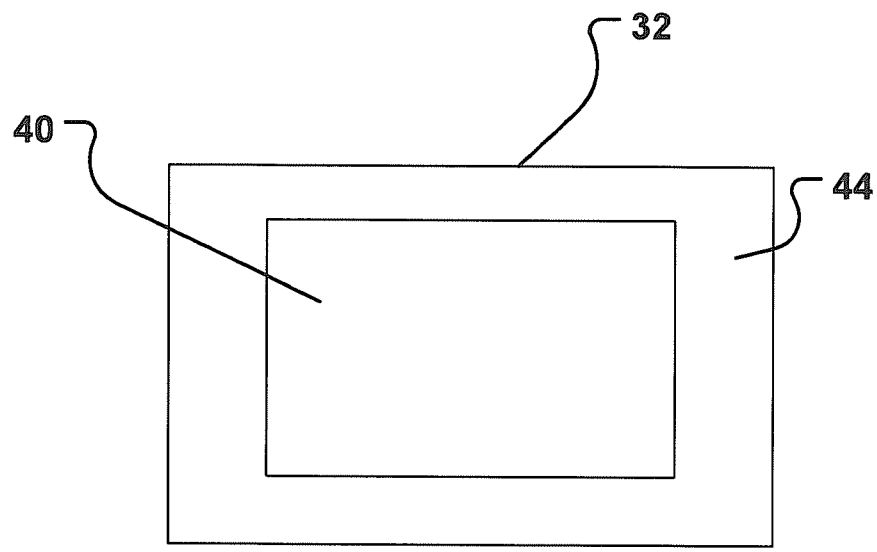
FIG. 4 is a schematic illustration of a first display with an image, wherein a second display is provided mutatis mutandis.

As seen in FIG. 4 the size of the first visual presentation 40 based on image data may be a proportion of the screen size 44 of the first display 32. The same applies to the second visual presentation, namely that the size of the second visual presentation based on image data may be a proportion of the screen size of the second display 34. Usually the relation between physical screen size and size of the image displayed thereon is opposite, i.e. a proportion of the screen size occupied by the displayed image is less than the size of the larger screen. A superimposed common image comprises the images from both the first display unit 32 and the second display unit 34 via the semi-transparent mirror 36.

Some embodiments utilize smaller screen units, such as wearable glasses with individual displays, such as miniature monitors or screens, for each eye to achieve the superimposed common image that is to be perceived by the patient. Each display for these embodiments is in close proximity with respectively eye and directed specifically towards the same, thus no mirror is needed and the image is superimposed in the visual cortex of the person wearing the glasses. The individual visual impression from each eye is processed by the brain. For these embodiments the blocking device may be omitted as individual information is presented to each eye.

The patient 31 is positioned in front of the set-up and focuses on the superimposed common image on the mirror 36. This focusing on the common image is done unconsciously by the patient. The superimposed common image is perceived by the person on a virtual 2-D surface, moreover, this 2-D surface is perpendicular to the vision axis of the person.

The first and second display 32, 34 may show a first image and a second image either as identical images of which for instance only the spatial position is modified during a training session.

Alternatively, or in addition, the image contents of the first image and the second image may differ.

For instance, the visual presentation may be a stereoscopic image presentation that relies on the presentation of a slightly different first image and second image to each eye. A stereoscopic image presentation is based on a pair of 2-D images, namely the first image and the second image representing two perspectives of the same object, with a minor deviation similar to the perspectives that both eyes naturally receive in binocular vision. In this manner, a 3-D illusion may be created for patients having established or improved binocular vision starting from the pair of 2-D images, whereby depth perception is created in the brain based on the two images or the superimposed image. Hence, embodiments may take advantage of such 3-D images, but it is not necessary for all embodiments. In the present embodiment, the two images are presentable as a computerized stereogram, wherein the individual images are separated, e.g. by means of blocking device 35, such as glasses with differently polarized lenses, see FIG. 5.

At least a portion of the first image and the second image, or the superimposed image, may be a series of single image frames, such as a movie, or a computer program application, such as a text processing program or a spreadsheet program.

In order to initially calibrate the visual system to the patient, the patient is allowed to act on an input device 33. The boundary value is thus determined. Alternatively, an initial boundary value may be determined previously, e.g. by an optician, and provided as an initial boundary value.

For determining the boundary value, the input device 33 is arranged to register user input, for instance such as e.g. a button, joystick, microphone or any arbitrary input device. The input device 33 is used to register a response from the patient when the patient starts to experience a distorted vision, such as when the presented superimposed image as perceived as distorted. The input could for example be performed by pushing a button or by a sensor register a specific eye movement made by the patient or using the eye tracker. This distortion is provided by manipulating at least one vision parameter for first and/or second visual presentation shown to the patient. For instance, the first and second image are moved in opposite spatial directions, their size is changed individually, their sharpness is blurred, etc. When the patient looses binocular vision, i.e. sees double objects, the patient input is registered and thus the aforementioned boundary value is determined.

The image in the first and second visual field is for instance slightly separated from each other over a short period of time, as the image emerges on the superimposed common image. At a certain level of displacement of the images, depending on the individual and the severity of the eye disorder, the patient begins to loose binocular vision, i.e. sees double objects. The spatial displacement of the image is performed in this embodiment in two directions. To determine the maximum displacement value, the right hand-side-part image is displaced even further to the right vice versa for the left hand-side-part image. The minimum displacement value the right hand-side-part image is displaced to the left, in some sessions even beyond the left hand-side-part image vice versa for the left hand-side-part image. To properly define the boundaries for single vision, the calculation procedure may be repeated until satisfactory measurements are obtained. A mean value of several boundary values may thus be determined as the boundary value used in the subsequent procedure.

Thus, at this stage the interval of the Panum's fusional space 10 is determined by the apparatus 30 within the person specific boundaries, as now defined by the data of the boundary value available for further use in the system. This is illustrated in FIG. 1, at limit 11 and limit 15. From this value determined for the specific person, a therapy session boundary value is defined. The determination of a current boundary value may be repeated during a therapy session. This provides for an up-to date tuning of the therapy based on current determined values of the specific patient. In this manner, the therapy session takes the patient situation and condition into consideration, e.g. by lowering the boundary value when the patient becomes tired. Alternatively, or in addition, the therapy session may be automatically ended, when the boundary value is below a predetermined minimum value, i.e. when double vision occurs too quickly or early. In this case, the patient may continue to play the visually presented computer game or continue watching a movie, however with the manipulation of the vision parameter(s) disabled.

Then exercises are performed based on this boundary value. Training is made based on a specific proportional share of the boundary value of the person's capacity, i.e. a vision parameter is manipulated to a lesser degree than the boundary value, such that binocular vision is maintained during the training session as the Panum's fusional space 10 is not left. For instance, vision parameters are manipulated up to a value of approximately 70% of the determined boundary value. The specific ratio may be individually adapted in order to prevent fatigue or to avoid that the individual loose interest in doing the exercise, due to the task may be too demanding.

A ratio value between the maximum value of the first range value and the boundary value is in the interval from 0 to 1, preferably in the interval 0.6 to 0.95. The ratio value has a maximum value where efficiency of the perceptual motor learning for the patient does not occur or where efficiency of the perceptual motor learning for the patient is undetectable.

Additionally, or alternatively, as already mentioned, the first initial value for the boundary value could be based on and provided by an eye doctor or responsible therapist. The initial boundary value could also be determined through measurements performed by an eye doctor or responsible therapist. The boundary value could thereafter be individually determined and subsequently updated during the training session. The update may be based on input from the patient or the patient's treatment history or measurements performed during the training session. The updates of the boundary value could be controlled to follow the patient's development or the patient's treatment history. An individually adapted boundary value is used in order to prevent fatigue or to avoid that the individual looses interest in doing the exercise.

The longer a training session lasts, the more tired the patient gets and it is therefore provided to adjust the first range in dependence of the training time, e.g. descending the first range over time, to compensate for fatigue or tiredness.

Some embodiments include an eye tracker 38 for both the right hand-side part and a left hand-side part of the visual system. The tracker and the display are linked to each other such that the information from eye tracker yields information regarding the amount of displacement of the image on the display. The processing unit may thus be adapted to asses the information from the eye tracker and divert the output to the corresponding display. In some embodiments an eye-tracking functionality asses a potential amount of strabismus of the patient as an input concerning the progress of the vision therapy. Based on this spatial information the image of the display, which corresponds to the eye with the miss-aligned visual axis, may be changed to counter-act the miss-alignment.

Separating the two individual images on the superimposed common image based on the individual visual presentations of the first and second display unit 32, 34 further apart stimulates increased convergence. Moving the two individual images closer makes convergence easier.

The processing unit 39 puts variation to this superimposed common image by oscillating, or fluctuating the visual presentations based on image data, i.e. pictures, images, etc. For instance a back and forth relative motion of the images, i.e. the individual visual presentations of the first and second display unit 32, 34, is performed. The range of movement is kept within the above portion of the boundary value, so that binocular vision is maintained, but varied. In this manner the eyes are trained to converge and diverge during the therapy session. This superimposed fluctuation of the image in the first and second visual field displaces the image slightly within respectively display around a predefined separation level where the two images are no longer on the same screen position of the virtual screen where the superimposed common image is shown. To which degree the image will oscillate is set by the calibration made by the patient, and the maximum range being a portion of the boundary value, as explained above. This enables the exercises to follow the person's progress in the therapy in both directions. If the person is tired, has les concentration, or is weak one day, the processing unit puts the requirements on a lower level, and vice versa. The processing unit is following the advancement when the patient condition improves and binocular vision capability is getting stronger and stronger.

In addition, the displacement of the image for each visual field, i.e. the first and second field, may be chosen to be below a predefined distance amplitude, i.e. a maximum distance value, as to secure the image does not get distorted by truncation due to e.g. physical dimensions of the first and second display or the physical dimension of the mirror. Otherwise the efficiency and relevance of the eye training may get diminished due to the fact that the patient's visual cortex will process information of the two individual images not fully aligned with each other (Panum's fusional space 10 would be left).

Figure 6:
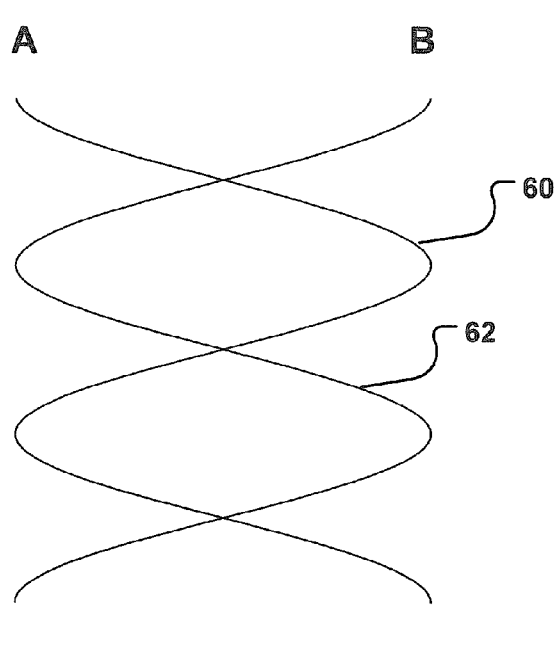
FIG. 6 is illustrating continuous fluctuation functions for each of the visual fields as they are overlapping each other to provide a varying degree of a superimposed common image.
Figure 7:
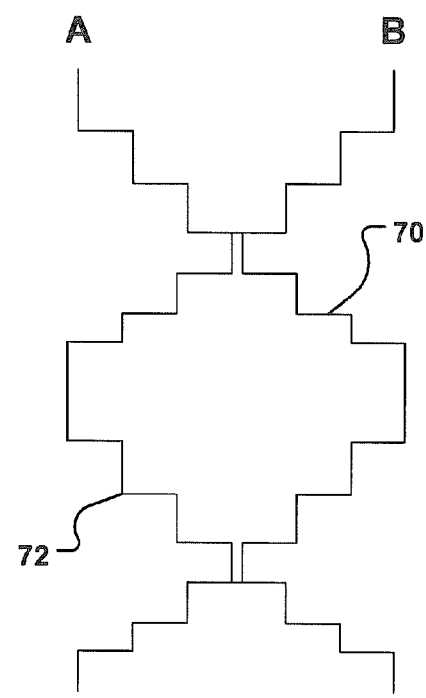
FIG. 7 is illustrating discontinuous fluctuation functions for each of the visual fields as they are overlapping each other to provide a varying degree of a superimposed common image.

In other embodiments, other physical circumstances may alternatively or in addition be of relevance to restrain the fluctuation of the images depending on the parameter to fluctuate. The spatial displacement of the image on each of the image units 32, 34 is controlled by the processing unit 39 by oscillating the image based on a fluctuation as a function of time. This fluctuation function may in some embodiments of the invention be a continuous reciprocating function, e.g. a sinusoidal function as shown in FIG. 6. Alternatively, the fluctuation function may be a discontinuous reciprocating or stepwise function, e.g. as shown in FIG. 7. Other waveforms for the fluctuation functions are possible e.g. square, triangle and sawtooth or any combination thereof or even irregular periodic waveforms.

In addition, pause times may be provided between series of fluctuation. Pause times may provide for a recovery of a tired patient in terms of binocular vision. Thus, extended therapy sessions may be provided compared to sessions where perceptual motor learning is performed continuously.

The time period for the oscillating fluctuation function is beneficially more than 1 second, i.e. a frequency below 1 Hz, for the reciprocating function. Examples for suitable frequencies, with beng limited to these specific frequencies, are for instance in the range from 0.1 to 0.9 Hz, such as 0.1; 0.2; 0.3; 0.4; 0.5; 0.6; 0.7; 0.8; or 0.9 Hz. With shorter time periods the demands on the individual suffering from an eye disorder may become too large, which might lead to undesired or ineffective perceptual motor learning.

As seen in FIGS. 6 and 7, the image in the first visual field A is fluctuating following function 60, while the image in the second visual field B follows function 62, respectively 70 and 72. The fluctuating curve function applies in particular to the spatial position of the respective image. Either of the parameters amplitude, frequency and the overlap of the functions may in some embodiments be predefined by the ophtamologist and/or the health provider. For the discontinuous fluctuation function the step size and duration of each step may also be predefined by the orthoptist and/or the health provider. A fully interactive visual apparatus may in some embodiments fully adapt these parameters to match the need and demands of the patient's eye disorder to fully achieve adequate and efficient eye training and exercise session.

The fluctuation function may be applied to various vision parameters, singly or in combination, to provide the perceptual motor learning. Preferably, the fluctuation is first, or only, applied to the spatial parameter. In addition to that other parameters may be modified accordingly.

The processing unit performs different types of tasks depending on the requests of the session, such as pictures, movies and computer games or any other arbitrary images displayable by electronic means. The movies and games are interesting for themselves for the patient, and the images, pictures, or movies may have an interactive audio component to them. A voice asks for instance a couple of simple questions about the picture, in order to provide that the patient does not loose concentration or focus from the visual presentation during the therapy session. The patient may thus provide a valuable feedback that the exercise is efficiently followed during the session. This data may be saved for later use.

The processing unit 39 further incorporates the capability to intermittent store patient related data concerning the individual's specifications as treatment settings and also for the ongoing training session. Such patient related data may comprise patient performance data including a value on the displacement where the individual loose binocular vision, and therapy session data, including specifications thereof as e.g. start time, duration of the session, number of calibrations performed, what type of exercise, movie, game, picture and so on. All stored data is logged with a time indication and available for further processing or action.

Prior to start of the exercise and training session the individual have to identify him/her self to the computerized image manipulation apparatus. This identification may for instance be performed by either a hardware token e.g. an usb-stick, smart card, or an software token e.g. an individual code entered to the apparatus using a keypad or keyboard, and/ or by using biometric data, e.g. finger print, retina recognition etcetera. When the individual is properly identified, the specific settings are loaded into the processing unit that controls the image manipulation. The computerized image manipulation apparatus is now attuned to the needs and demands of the individual commencing the session.

Moreover, the processing unit 39 may has communication ability for down/up-loading specification and stored information to a centralized common database. The centralized common database is preferably reachable via the Internet using TCP/IP. When, as described above, the individual logs into the apparatus, a communication channel opens to the centralized common database and checks and/or retrieves settings for the individual. If new information and settings are to be updated these are downloaded and loaded into the processing unit that controls the image manipulation. After the exercise and training session is completed the gathered performance data, e.g. intermittently stored on the processing unit 39 or in another memory of the apparatus 30 (not shown) during the therapy session, is uploaded to the centralized common database. The communication ability for down/up-loading provides for e.g. the health provider to interactively communicate with the patient and/or to post a message to the patient. The message will be displayed during the next session or sessions initiated by the patient.

The centralized common database facilitates base data and supporting evidence to be analyzed in respect of further develop the computerized image manipulation apparatus by e.g. changing initial settings depending of the status of the eye disorder for a population. For instance, compliance of the patient to the prescription can be more easily monitored remotely using the centralized common database by checking specific data, which is cost effective and potentially more reliable the e.g. an interview of the patient. Furthermore, by the centralized common database each computerized image manipulation apparatus is tracked and surveyed in order to e.g. avoid breakdowns or detect any potential faults. Updating the computerized image manipulation apparatus may also be possible by utilizing the information in the centralized common database.

Figure 8A:
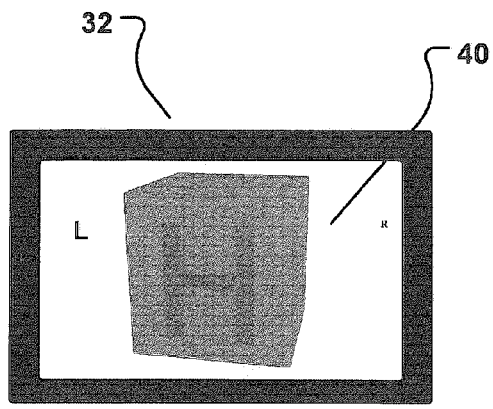
FIG. 8 is showing an image for respectively visual field, i.e. a) a right eye and b) a left eye, or vice versa.
Figure 8B:
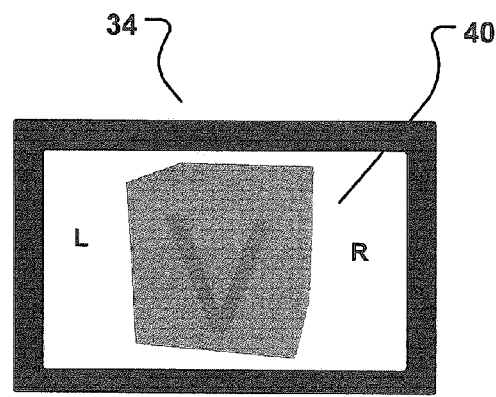
Figure 9A:
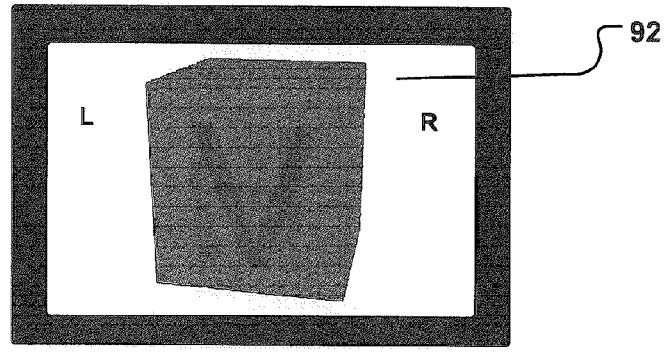
FIGS. 9a and b are showing a superimposed common image a) without blocking device, and b) with a partly overlapping blocking device.
Figure 9B:
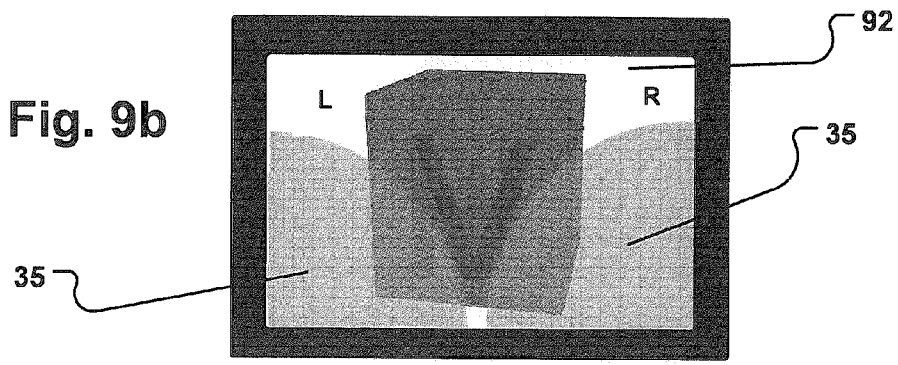

An example of an image is shown in FIG. 8a and FIG. 8b where in FIG. 8a an example of the image for the first screen 32 is shown, which e.g. is directed for perception by the right eye. In FIG. 8b an example of an image is shown for the second screen 34, which e.g. is directed towards the left eye. By superimposing the first and the second visual field to a single visual field, an image is shown as illustrated in FIG. 9a, the common superimposed image 92. This common superimposed image 92 may be split into the individual images for each eye by means of using the blocking device 35, whereby a separation of the visual fields is maintained, as illustrated in FIG. 9b. The effect of the blocking device 35 for the left eye respectively the right eye, is illustrated in the circular sectors in the lower corner of FIG. 9b at respectively side thereof. Thus the right and left eye of the patient will only receive the expected image as the non-intended image is blocked to enter respectively eye, i.e. retina. Alternatively, individual visual presentations may be provided to each eye, e.g. by the aforementioned glasses with miniature screens, whereby the blocking device may be omitted. The indications R and L in FIGS. 8a, 8b, 9a and 9b are for illustrative purposes only, and indicate the first and the second screen, respectively, i.e. the right and left screen in the example. The indicators are part of the image contents and are neither shown nor necessary for the actual implementation of the embodiment herein discussed. The image contents of images or visual information present therein is irrelevant in embodiments. However, specific image contents of images may allow for easy identification of objects, be undemanding or non-straining and thus easy to watch, easy to focus on, etc., which might be convenient in some cases.

While the initial settings are determined for a degree of strabismus and/or a degree of amblyopia, training can effectively be performed and the variation of the vision parameters is is performed. For instance, on the display which corresponds to the dominant eye, i.e. non-amblyoptic eye, the image is changed back and forth between a sharp clear image and a slightly blurred, i.e. a vague or less distinct, image. This small continuously change of sharpness diverts the visual cortex to assess more of the image from the retinal image of the amblyoptic eye. Over a time period with daily sessions of training, the visual cortex will equate the image processed between the eyes. As a result of this perceptual motor training, the patient will gradually get additional or improved visual perception as e.g. depth perception. Several other image and/or vision parameters may be used in this respect for suitable manipulation by image processing e.g. the color information, fading the color image back and forth between full color and a grayscale image. Alternatively or in addition, the manipulation may comprise to manipulate vision parameters, such as a specific color component in the presented image. Alternatively or in addition, at least a portion of one of the presented images may be actively faded out either in respect to the other image, or by changing the intensity on either image in respect to the other. Alternatively or in addition, either image may be blurred or modified in terms of sharpness in respect to the other image, to mention a few options.

Some embodiments may manipulate different vision parameters in respect to respectively eye, while other embodiments use and manipulate the same vision parameter for both eyes. Alternatively or in addition, only the vision parameter for one of the eyes is manipulated to achieve the result of perceptual motor training.

Image processing may comprise manipulation of vision parameters of visual presentations, e.g. based on image data, such as spatial parameters including dimension or position of an image, or purely vision parameters, such as defocus, fading, color change, intensity, and/or illumination. Image processing in this context also comprises movement, displacement, rotation, position, size and other types of spatial operation of the image on the screens. For these parameters the threshold value, as discussed above, reflects the physical limitation for the particular parameter chosen in regard to the specification of the equipment for that parameter. To restrain the parameter within the specification boundaries the efficiency of the exercise is maintained as the image is not truncated in a way that it disturbs the visual system of the patient.

Moreover, to establish and/or improve binocular vision a method is provided using the above described apparatus, for providing perceptual motor learning for the visual system of a patient having a binocular vision disorder. The method comprises manipulating at least one first and second vision parameter related to a visual presentation directed towards to each eye, respectively. By determining a boundary value of a vision parameter for the manipulation, where binocular vision disappears for the patient, a manipulating, including oscillating or fluctuating, of the vision parameter is controlled within a first range below the boundary value. Furthermore, the first range having a maximum value that is less than the boundary value, the perceptual motor learning is effective without unnecessarily tiring the patient during a therapy session.

The described embodiments may be at least partly implemented by means of a computer program. The computer program may be provided to enable carrying out some steps of the method of perceptual motor learning according to the above. A computer-readable medium having embodied thereon the computer program for processing by a computer for establishing and/or improving binocular vision is provided. The computer program comprises a plurality of code segments for a first and a second manipulation of at least one vision parameter for respectively manipulation, related to a visual presentation directed towards each eye, respectively. Code segments may be provided for facilitating determining a boundary value of the vision parameter for the first and/or second manipulation, where binocular vision disappears for the patient. A range of manipulating vision parameters may for instance automatically increased during determination until patient input is made at the boundary value. Alternatively, the boundary value may be determined previously and provided, e.g. in a memory, to a code segment of the computer program for processing. Further, code segments are provided for controlling the manipulating, including oscillating or fluctuating, of first and/or second vision parameter within a first range, where the first range having a maximum value that is less than the boundary value, for the perceptual motor learning.

Figure 10:
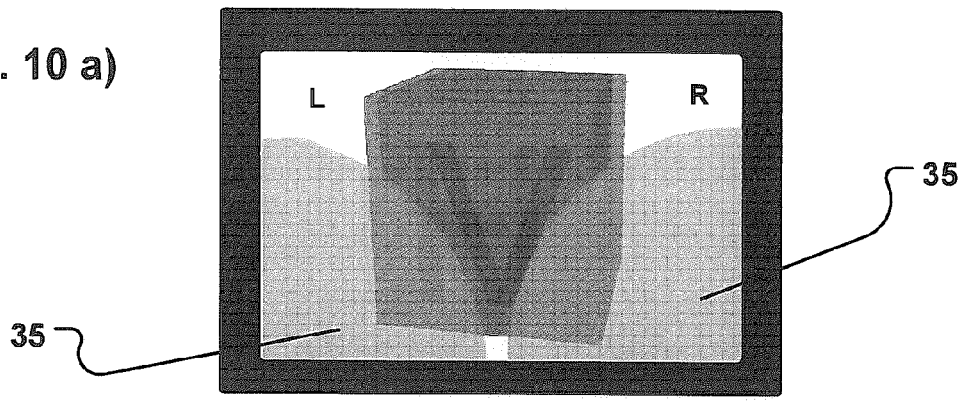
FIGS. 10a-h are illustrating a sequence of consecutive partly superimposed common images a)-h) where the first and second image are spatially displaced with a greater distance for each subsequent superimposed common image.
Figure 10:
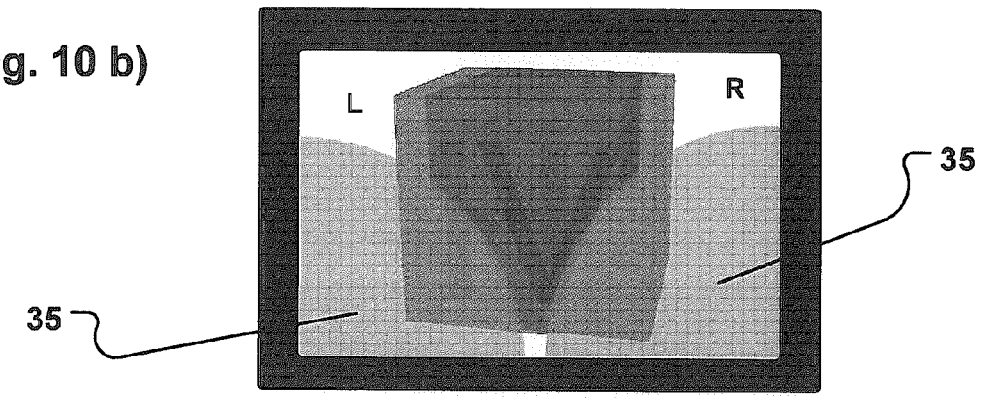
Figure 10:
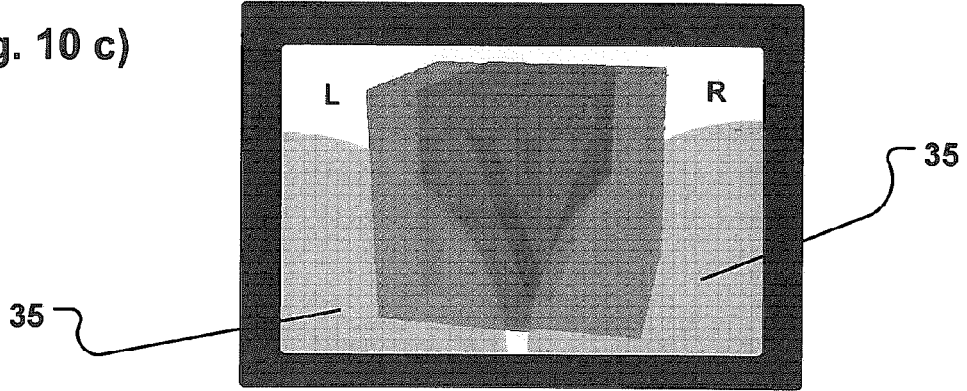
Figure 10:
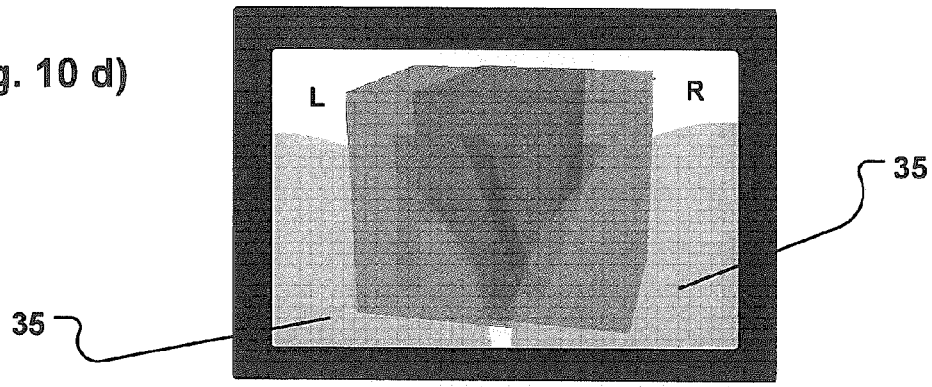
Figure 10:
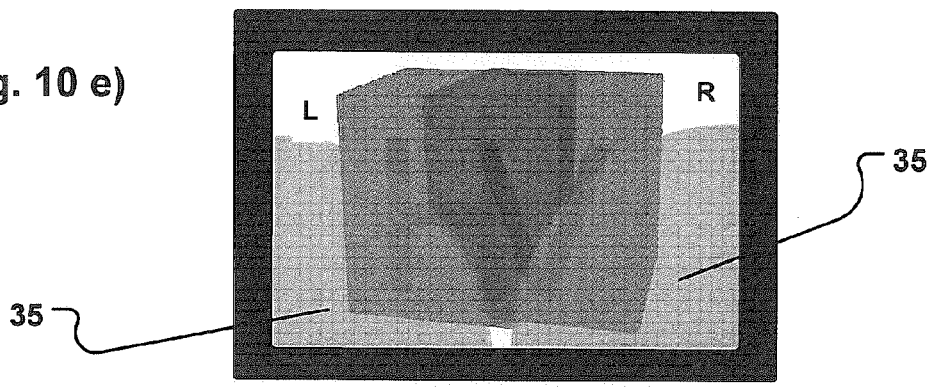
Figure 10:
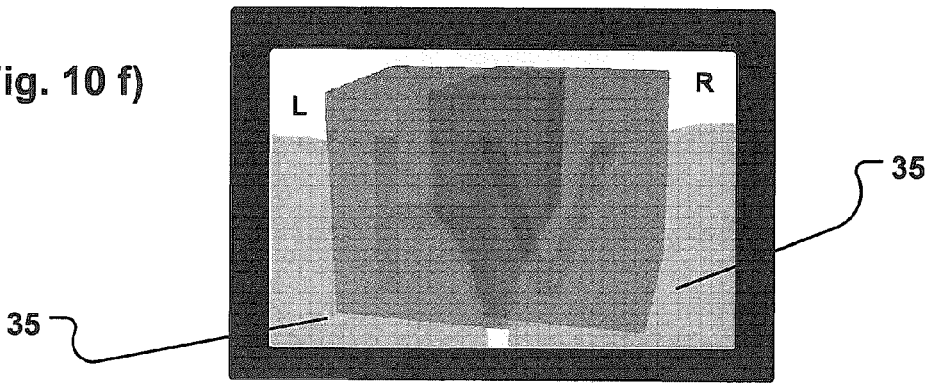
Figure 10:
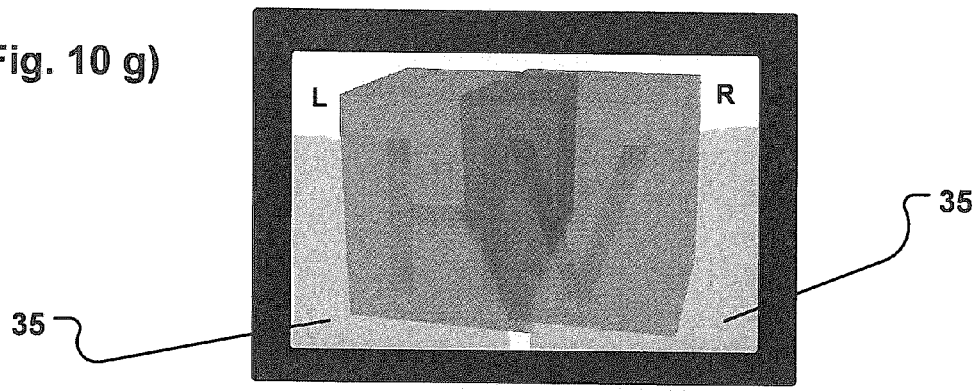
Figure 10:
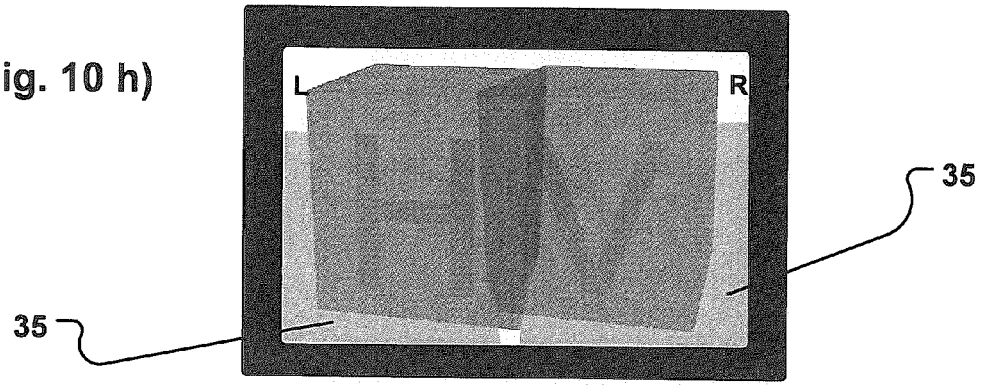

While the brain and the individual have experienced the additional image, the next process is to attend to the heterotropic eye, the miss-alignment of the visual axis. On the display which corresponds to the miss-aligned eye the imaged is spatially changed back and forth towards the direction for an individual having two parallel visual axes. The small change of the image on the two dimensional display affects the visual cortex processing the presented visual presentation or image as to intermittently lose e.g. the depth perception. As the individual has previously experienced the additional image the brain is trying to regain the lost information. And as the changes are minute and the ocular-motor system engages the eye muscles to effectively counteract the loss and regain the information. A sequence of superimposed common images is shown in FIG. 10 $a$-$h$. Images from the first and second visual field are aggregated and slightly displaced in respect to each other, wherein the smallest distance is shown in FIG. 10$a$ and the largest in FIG. 10$h$. The effect of the blocking device 35 is less visualized as in the earlier part for this sequence example, due to illustrative limitations. Over a period of time the displacement of the image on the display corresponding to the heterotropic eye will be less pronounced. This will however be a gradual change as it is necessary to perform the eye training on the verge between fully visual perception and slight losing the same. The indications R and L in FIG. 10 $a$-$h$ are for illustrative purposes only, they are neither shown nor necessary for the actual implementation of the embodiment herein discussed.

Clinical trials using the above described computer based image manipulation under confidentiality has confirmed a positive treatment effect for treatment of decompensated phorias (i.e. phorias that give rise to symptoms). Individuals with an eye disorder categorized in the largest subgroup of decompensated phorias, convergence insufficiency (CI) was subject in the trial. The computer based orthoptic training was conducted during at least 4 weeks.

From the results the near point of convergence improved, as well as the prism base out convergence ability at near, both these results was statistically significant. Conclusion is that the computer based orthoptic training as mention above improves convergence ability for individuals with CI. Moreover, the training effect is similar to what can be expected in about 8 weeks with traditional treatment. A duration of a treatment period need on average to be longer than the performed clinical trial period to permanently affect the vergence function to reach normal values for the participating individuals.

The above described computer based image manipulation exercise the plasticity of the brain in respect of interpretation of visual information provided uniquely for each eye, respectively. Due to the prevailing eye disorder for the individual it is expected that the training shows a hysteresis curve between the eyes. By utilizing this effect and following its properties over time on an individual level, the efficiency of exercise will become more specified adapted for the specific individual both in respect of the eye disorder and in respect of the individual's development. Moreover, the centralized common database may incorporate for some embodiments opportunities to estimate the exercise and training efficiency based on a population taken into account of this hysteresis in the visual system, thus providing a general knowledge to optimize the training to better accommodate a normal vision.

It has further been realized that the invented apparatus and method may in addition be used for the purpose of being a support tool for diagnosing eyes related problems or disorders. Examples of diagnosis facilitated by the apparatus could be: loss of sight—for example due to retinal detachment; eyes resolution; eyes resolution with respect to depth; loss of vision due to damage or progressive destruction of or the around the macula; color vision; measure of damage to the macula—e.g. due to welding; peripheral vision; linearity of the visual field—e.g. mesh; scotopic, mesopic or photopic vision; contrast vision; etc.

Depending on how much the results of these diagnostic tests deviate from what can be seen as normal for a healthy person, they can be basis for a recommendation that the patient should attend to follow-up examination, e.g. with a visit to an eye doctor, for confirming the diagnosis made and to take treatment measures. The tests are preferably computer based. The tests are preformed by the computer based apparatus and are designed and based around the patient reacting to images being shown on the screen. The diagnostic tests are to be performed in accordance with the instructions given before each test starts. Further, the diagnostic tests are preferably designed to be self explained so that each patient should be able to, as far as possible, perform them by him/herself without the help of an optician. The results from each diagnostic test will then be processed and presented in an appropriate form (e.g. chart, table, diagrams, graphically, etc.) to the patient and/or optician.

The diagnostic tests are either based on traditionally tests adjusted to work on the invented apparatus or are tests that the skilled person would envisage from the present disclosure, made specifically to be performed by the invented apparatus.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. Visual presentations may be based on image data, such as described above, when displayed on a screen. Alternatively, the visual presentation may has a basis in real illuminated objects presented to the eye, wherein vision parameters of the visual presentation are modifiable by optical means, e.g. spectacles that have controllable refractivity, tinting, color, etc. First and/or second units may in these embodiments be lenses or prisms on a spectacles arrangement. Alternatively or in addition, the first and/or second units are lenses or prisms on a spectacles arrangement and wherein the control unit is arranged to pivot the lenses or prisms on the spectacles arrangement in order to manipulate the visual presentation. The scope of the invention is only limited by the appended patent claims.

The invention claimed is:

1. An apparatus for establishing and/or improving binocular vision of a patient, wherein said apparatus is adapted to provide perceptual motor learning for the visual system of the patient having a first eye and a second eye and a binocular vision disorder, said apparatus comprising:
   a first display unit configured for providing a first manipulation of at least one first vision parameter of a visual presentation directed towards said first eye,
   a second display unit configured for providing a second manipulation of at least one second vision parameter of a visual presentation directed towards said second eye, and
   a processing unit configured to:
   provide or determine a boundary value for said first and/or second vision parameters for said first and/or second manipulation of said first and/or second vision parameter, where binocular vision disappears for said patient at said boundary value and
   control said first display unit and/or second display unit to provide an entire manipulation including an oscillation or a fluctuation of said first and/or second vision parameter only within a first range, said first range having a maximum value that is less than said boundary value and the ratio between said maximum value of said first range and said boundary value is in the interval from 0.6 to 0.95.

2. The apparatus of claim 1, wherein said processing unit is configured to provide or determine a plurality of boundary values for a plurality of said first and/or second manipulations of said first and/or second vision parameters, where binocular vision disappears for said patient at each of said boundary values.

3. The apparatus of claim 1, wherein the oscillation or fluctuation is selected from the group consisting of a continuous-reciprocating, a discontinuous function, and a stepwise reciprocating function.

4. The apparatus of claim 1, wherein said manipulation of said first and/or second vision parameter within a first range comprises an oscillation and wherein said oscillation has an amplitude that is equal to or less than said maximum value of said first range, and/or wherein said oscillation has a frequency.

5. The apparatus of claim 4, wherein said oscillation in said first and/or said second display unit is a continuous oscillation function, and wherein said continuous oscillation function for said first display unit is optionally different than for said second display unit.

6. The apparatus of claim 1, wherein said first and/or second manipulation of said first and/or second vision parameters comprises inducing a movement, a displacement, a rotation, a position, or a size of the visual presentation.

7. The apparatus of claim 1, wherein said first and second manipulation involves an image processing operation, and wherein said visual presentation is based on image data; and wherein said image data is identical or non-identical for said first and said second display units and wherein said image data comprises an image or a movie configured for electronic display.

8. The apparatus of claim 7, wherein said image data additionally comprises an interactive audio component.

9. The apparatus of claim 8, wherein said first and/or second manipulation of said first and/or second vision parameter comprises a fluctuation of said vision parameter of said image data and
   wherein said fluctuation of said vision parameter in said first display unit is aligned to said fluctuation of said vision parameter in said second display unit, or wherein said fluctuation of said vision parameter in said first display unit is aligned arbitrary to said fluctuation of said vision parameter in said second display unit.

10. The apparatus of claim 1, wherein said first unit and/or said second unit are adapted to bring said visual presentation in alignment with a visual axis of the first eye and a visual axis of the second eye, respectively.

11. The apparatus of claim 1, wherein said processing unit is adapted to oscillate or fluctuate only one single vision parameter, and further vision parameters different from said one single vision parameter are kept constant during a perceptual motor learning session.

12. The apparatus of claim 1, wherein said processor is configured to update said first range based on an input from said patient to follow an improvement in binocular vision of said patient.

13. The apparatus of claim 1, wherein said first range descends from a start value that is updateable over time during a training session to compensate for patient fatigue during an ongoing perceptual motor learning session.

14. The apparatus of claim 1, further comprising a diagnostic support tool unit configured for detecting or measuring retinal detachment, resolution, resolution with respect to depth, vision loss, macular damage, color vision, peripheral vision, linearity visual field, scotopic vision, mesopic vision, photopic vision and/or contrast vision.

15. The apparatus of claim 1, wherein said first and/or second manipulation of said first and/or second vision parameters is a manipulation of an entire visual presentation or wherein said first and/or second vision parameters are modified only in a portion of said visual presentation.

16. The apparatus of claim 7, wherein said first and/or second vision parameter is selected from the group consisting of focus, colour, illumination, size, orientation, position of an image or combinations thereof.

17. The apparatus of claim 1, wherein said manipulation of said first and/or second vision parameter within a first range comprises a fluctuation and wherein said fluctuation in said first display unit and said display second unit follows a discontinuous fluctuation function, and wherein said discontinuous fluctuation function optionally has a predetermined step height or an arbitrary step height; and wherein said discontinuous fluctuation function for said first display unit is optionally different than for said second display unit.

* * * * *